(12) United States Patent
Sorimoto et al.

(10) Patent No.: US 10,039,475 B2
(45) Date of Patent: Aug. 7, 2018

(54) INTRAORAL THREE-DIMENSIONAL MEASURING DEVICE, INTRAORAL THREE-DIMENSIONAL MEASURING METHOD, AND INTRAORAL THREE-DIMENSIONAL MEASUREMENT RESULT DISPLAY METHOD

(71) Applicant: J. MORITA MFG. CORP., Kyoto (JP)

(72) Inventors: Keisuke Sorimoto, Kyoto (JP);
Mikinori Nishimura, Kyoto (JP);
Tsuyoshi Tanaka, Kyoto (JP);
Masayuki Sano, Kyoto (JP); Keiichi Tsuda, Kyoto (JP); Ryosuke Kaji, Kyoto (JP)

(73) Assignee: J. MORTIA MFG. CORP., Kyoto (JP)

( * ) Notice: Subject to any disclaimer, the term of this patent is extended or adjusted under 35 U.S.C. 154(b) by 23 days.

(21) Appl. No.: 15/209,379

(22) Filed: Aug. 11, 2016

(65) Prior Publication Data

US 2017/0202483 A1    Jul. 20, 2017

(30) Foreign Application Priority Data

Jul. 13, 2015    (JP) .................................. 2015-139541

(51) Int. Cl.
*G01B 11/24*    (2006.01)
*A61B 5/107*    (2006.01)
(Continued)

(52) U.S. Cl.
CPC .......... *A61B 5/1077* (2013.01); *A61B 1/0005* (2013.01); *A61B 1/00009* (2013.01);
(Continued)

(58) Field of Classification Search
CPC ... A61B 5/0088; A61B 5/1077; A61B 5/1079; A61B 1/24; A61B 1/0009; A61B 1/0005;
(Continued)

(56) References Cited

U.S. PATENT DOCUMENTS 9,198,627 B2 *  12/2015  Suttin .................. A61C 8/0001
9,301,692 B2 *   4/2016  Kaji ..................... A61B 5/0088
(Continued)

FOREIGN PATENT DOCUMENTS

DE    102012214473 A1    2/2014
JP    2011-242178 A    12/2011

OTHER PUBLICATIONS

Extended European Search Report issued in corresponding European Application No. 16178883.1, dated Dec. 23, 2016 (6 pages).

*Primary Examiner* — Hoa Pham
(74) *Attorney, Agent, or Firm* — Osha Liang LLP

(57) ABSTRACT

An intraoral three-dimensional measuring method, comprising: acquiring, with a handy scanner, wide range three-dimensional measurement information on a three-dimensional shape measured on a wide range in a desirable measurement range in an intraoral space; acquiring, with the handy scanner, a plurality of pieces of narrow range three-dimensional measurement information each on a three-dimensional shape measured on a narrow range narrower than the wide range in the measurement range; and locating, with a controller, the plurality of pieces of narrow range three-dimensional measurement information based on the wide range three-dimensional measurement information by use of, as a synthesis reference, intra-measurement range position information common to the wide range three-dimensional measurement information and each of the plurality of pieces of narrow range three-dimensional measurement information, and creating synthetic three-dimensional information on the measurement range.

18 Claims, 11 Drawing Sheets

(51) Int. Cl.
  *G01B 11/25* (2006.01)
  *A61B 1/24* (2006.01)
  *A61C 9/00* (2006.01)
  *A61B 5/00* (2006.01)
  *A61C 19/04* (2006.01)
  *A61B 1/00* (2006.01)

(52) U.S. Cl.
  CPC .............. *A61B 1/24* (2013.01); *A61B 5/0088* (2013.01); *A61B 5/1079* (2013.01); *A61C 9/0053* (2013.01); *A61C 19/04* (2013.01); *G01B 11/2518* (2013.01)

(58) Field of Classification Search
  CPC .... G01B 11/2518; A61C 9/0052; A61C 19/04
  USPC .................. 356/601–623; 600/425; 702/152; 433/29
  See application file for complete search history.

(56) References Cited

U.S. PATENT DOCUMENTS

| | | | | |
|---|---|---|---|---|
| 2006/0246393 | A1* | 11/2006 | Eiff | A61C 1/00 433/98 |
| 2010/0145189 | A1* | 6/2010 | Hintersehr | A61C 9/0053 600/425 |
| 2014/0146142 | A1 | 5/2014 | Duret et al. | |
| 2014/0365140 | A1 | 12/2014 | Popilka et al. | |
| 2015/0320320 | A1* | 11/2015 | Kopelman | A61B 5/0088 433/24 |
| 2017/0289523 | A1* | 10/2017 | Lee | H04N 13/0207 |

\* cited by examiner

INTRAORAL THREE-DIMENSIONAL MEASURING DEVICE, INTRAORAL THREE-DIMENSIONAL MEASURING METHOD, AND INTRAORAL THREE-DIMENSIONAL MEASUREMENT RESULT DISPLAY METHOD

TECHNICAL FIELD

The present invention relates to an intraoral three-dimensional measuring device and an intraoral three-dimensional measuring method for capturing an image of light directed toward an intraoral measurement target such as, for example, a tooth and performing an image analysis process to measure a three-dimensional shape of the measurement target, and also relates to an intraoral three-dimensional measurement result display method.

BACKGROUND ART

Devices and methods for measuring a three-dimensional shape of a measurement target by any of various methods such as, for example, a light-section method, a focus method, a spatial coding method, a phase shift method, a stereo method, a photogrammetric method, a SLAM method and the like have been proposed and put into practice. For example, a shape measuring device described in Patent Document 1 is operated as follows. Light for projection passes a lattice-pattern plate to be lattice-pattern light. This light is projected onto, and reflected by, a measurement target. An image of the reflected light is captured. Based on the image, a three-dimensional shape of the measurement target is measured. In the field of dental treatment in recent years, such a shape measuring device is used to measure a three-dimensional shape of a dental arch. Thus, such a shape measuring device is applied for, for example, producing artificial teeth and designing prostheses.

However, the measuring device described in Patent Document 1 (measuring device Z in FIG. 11A) is not usable to measure, for example, the entirety of a dental arch Da, which expands over a wide measurement range in an intraoral space, which is narrow, at one time. The reason is as follows. The dental arch as the image capturing subject has a complicated shape, and there are many dead angles in the case where image capturing is performed merely once. The resultant three-dimensional data has many missing parts.

For the above-described reason, the measurement needs to be performed as follows. As shown in FIG. 11A, a plurality of narrow ranges Rn, each of which is a part of the measurement target, are measured (hereinafter, referred to as "narrow range measurement"). The narrow ranges Rn are defined such that the narrow ranges Rn cover the entirety of the wide measurement target and also such that adjacent narrow ranges Rn have overlap portions Rr. FIG. 11B shows narrow range measurement results In'. As shown in FIG. 11C, the adjacent narrow range measurement results In' are joined together based on the overlap portions Rr. As a result, an entire measurement result Ic' is acquired as the measurement result on the entirety of the wide measurement target.

However, when two adjacent narrow range measurement results In' are joined together, there occurs an error although being small. As shown in FIG. 11D, when such adjacent narrow range measurement results In' are joined together sequentially to form the entire measurement result Ic', such small errors are accumulated. As a result, the entire measurement result Ic' may undesirably have a large error.

CITATION LIST

Patent Literature

Patent Document 1: Japanese Laid-Open Patent Publication No. 2011-242178

SUMMARY OF THE INVENTION

According to one or more embodiments of the present invention an intraoral three-dimensional measuring device and an intraoral three-dimensional measuring method can accurately perform three-dimensional measurement on a wide measurement range in an intraoral space, which is narrow, and also an intraoral three-dimensional measurement result can be displayed.

According to one or more embodiments of the present invention, an intraoral three-dimensional measuring method includes acquiring, with a handy scanner, wide range three-dimensional measurement information on a three-dimensional shape measured on a wide range in a desirable measurement range in an intraoral space; acquiring, with the handy scanner, a plurality of pieces of narrow range three-dimensional measurement information each on a three-dimensional shape measured on a narrow range narrower than the wide range in the measurement range; and locating, with a controller, the plurality of pieces of narrow range three-dimensional measurement information based on the wide range three-dimensional measurement information by use of, as a synthesis reference, intra-measurement range position information common to the wide range three-dimensional measurement information and each of the plurality of pieces of narrow range three-dimensional measurement information, and creating synthetic three-dimensional information on the measurement range.

According to one or more embodiments of the present invention, an intraoral three-dimensional measuring device includes a handy scanner that acquires wide range three-dimensional measurement information on a three-dimensional shape measured on a wide range in a desirable measurement range in an intraoral space, and a plurality of pieces of narrow range three-dimensional measurement information each on a three-dimensional shape measured on a narrow range narrower than the wide range in the measurement range; and a controller that locates the plurality of pieces of narrow range three-dimensional measurement information based on the wide range three-dimensional measurement information by use of, as a synthesis reference, intra-measurement range position information common to the wide range three-dimensional measurement information and each of the plurality of pieces of narrow range three-dimensional measurement information, and creates synthetic three-dimensional information on the measurement range.

The wide range in a desirable measurement range described above may be the entirety of the desirable measurement range, a part of the desirable measurement range that is wider than the narrow range, or an entire measurement range formed by joining a plurality of pieces of three-dimensional measurement information on parts of the desirable measurement range that are each narrower than the wide range and wider than the narrow range, the joining being performed at an overlapping portion of each piece of three-dimensional measurement information.

The measurement range may be the entirety of the dental arch including the gum in the intraoral space, a predetermined region of the dental arch, or the entirety of, or a part of, edentulous jaw.

The wide range three-dimensional measurement information, the narrow range three-dimensional measurement information, and the synthetic three-dimensional information described above may be numerical information such as spatial coordinate information, direction vector information of texture, reliability information on the measured value or the like, or image information.

According to one or more embodiments of the present invention, three-dimensional measurement on the wide measurement target in the narrow intraoral space is accurately performed.

This will be described in more detail. According to the above-described method, wide range three-dimensional measurement information on a three-dimensional shape measured on a wide range in a desirable measurement range in an intraoral space, and a plurality of pieces of narrow range three-dimensional measurement information each on a three-dimensional shape measured on a narrow range narrower than the wide range in the measurement range, are acquired. The plurality of pieces of narrow range three-dimensional measurement information are located based on the wide range three-dimensional measurement information by use of, as a synthesis reference, intra-measurement range position information common to the wide range three-dimensional measurement information and each of the plurality of pieces of narrow range three-dimensional measurement information, to create synthetic three-dimensional information on the measurement range. The synthetic three-dimensional information on the measurement range created in this manner includes the narrow range three-dimensional measurement information based on the wide range three-dimensional measurement information. Thus, three-dimensional measurement on the entirety of the measurement range is accurately performed with no accumulation of errors.

According to one or more embodiments of the present invention, the wide range three-dimensional measurement information may be used to create wide range three-dimensional image information on the three-dimensional shape of the wide range; the plurality of pieces of narrow range three-dimensional measurement information each may be used to create narrow range three-dimensional image information on the three-dimensional shape of the narrow range; and when the synthetic three-dimensional information is created, synthetic three-dimensional image information may be created based on the synthetic three-dimensional information.

Alternatively, the synthetic three-dimensional information creation unit may create synthetic three-dimensional image information based on the synthetic three-dimensional information.

According to one or more embodiments of the present invention, the measurement information is displayed as an image. This allows the user to make an operation while visually checking the measurement state, and thus improves the operability.

According to one or more embodiments of the present invention, the plurality of pieces of narrow range three-dimensional measurement information may be measured at a higher resolution than that of the wide range three-dimensional measuring information.

According to one or more embodiments of the present invention, the resultant synthetic three-dimensional information on the measurement range includes the narrow range three-dimensional measurement information of a high resolution based on the wide range three-dimensional measurement information with no accumulation of errors. Thus, three-dimensional measurement on the entirety of the measurement range is performed at high precision with a high resolution.

According to one or more embodiments of the present invention, when the synthetic three-dimensional information is created, the synthetic three-dimensional information may be created by use of, as intra-measurement range position information, characteristic portion information common to each of the plurality of pieces of narrow range three-dimensional measurement information and the wide range three-dimensional measurement information.

Alternatively, the controller may create the synthetic three-dimensional information by use of, as the intra-measurement range position information, characteristic portion information common to the each of plurality of pieces of narrow range three-dimensional measurement information and the wide range three-dimensional measurement information.

According to one or more embodiments of the present invention, the plurality of pieces of narrow range three-dimensional measurement information are accurately synthesized based on the wide range three-dimensional measurement information by use of the characteristic portion information to create the synthetic three-dimensional information.

According to one or more embodiments of the present invention, the intraoral three-dimensional measuring method may further include acquiring, with the handy scanner, position information on each of the plurality of pieces of narrow range three-dimensional measurement information and acquiring position information on the wide range three-dimensional measurement information. When the synthetic three-dimensional information is created, the synthetic three-dimensional information may be adjusted based on the acquired position information.

Alternatively, according to one or more embodiments of the present invention, the handy scanner acquires position information on each of the plurality of pieces of narrow range three-dimensional measurement information and acquiring position information on the wide range three-dimensional measurement information. The controller may adjust the synthetic three-dimensional information based on the acquired position information.

The position information described above may be position information based on an absolute position at the time of three-dimensional measurement as being acquired by the GPS, or position information based on a relative position with respect to, for example, the intraoral space. Therefore, the handy scanner described above may be a measurement device measuring an absolute position such as a GPS or the like or a measurement device measuring a relative position such as a position sensor or the like. Alternatively, the position information may be acquired by an acceleration sensor, a velocity sensor, a gyro sensor, an azimuthal sensor, a posture sensor, or a combination of any of these sensors.

According to one or more embodiments of the present invention, the synthetic three-dimensional information is adjusted based on the position information on each of the plurality of pieces of narrow range three-dimensional measurement information and position information on the wide range three-dimensional measurement information.

Therefore, the synthetic three-dimensional information is more precise and more accurate.

According to one or more embodiments of the present invention, when the synthetic three-dimensional information is created, a part of the wide range three-dimensional measurement information corresponding to each piece of narrow range three-dimensional measurement information may be overwritten with the each piece of narrow range three-dimensional measurement information.

According to one or more embodiments of the present invention, the information amount of the synthetic three-dimensional information is decreased.

According to one or more embodiments of the present invention, the wide range three-dimensional measurement information may be entire measurement information on a shape of the entirety of the measurement range.

According to one or more embodiments of the present invention, the resultant synthetic three-dimensional information has no accumulation of errors and is more accurate than synthetic three-dimensional information created in the case where a plurality of pieces of three-dimensional measurement information on ranges narrower than the wide range and wider than the narrow range are joined together at an overlapping portion of each piece of three-dimensional measurement information to provide wide range three-dimensional measurement information on the entirety of the measurement range.

According to one or more embodiments of the present invention, the intraoral three-dimensional measuring method may further include locating, with the controller, a plurality of pieces of the wide range three-dimensional measurement information by use of, as a joining reference, wide range position information common to adjacent pieces of wide range three-dimensional measurement information, and creating entire joining measurement information on the entirety of the measurement range.

According to one or more embodiments of the present invention, a plurality of pieces of wide range three-dimensional measurement information are located by use of, as the joining reference, wide range position information common to adjacent pieces of wide range three-dimensional measurement information, to create the entire joining measurement information on the entirety of the measurement range. Therefore, the synthetic three-dimensional information is created more accurately even on a wider measurement range.

According to one or more embodiments of the present invention, at least one of the plurality of pieces of the narrow range three-dimensional measurement information may be adjustment narrow range three-dimensional measurement information including measurement information on a part corresponding to the wide range position information; and the intraoral three-dimensional measuring method may further include adjusting, with the controller, the entire joining measurement information based on the adjustment narrow range three-dimensional measurement information.

According to one or more embodiments of the present invention, the entire joining measurement information on the entirety of the measurement range, created by locating the plurality of pieces of the wide range three-dimensional measurement information by use of, as a joining reference, wide range position information common to the adjacent pieces of wide range three-dimensional measurement information, is adjusted based on the adjustment narrow range three-dimensional measurement information. Thus, the entire joining measurement information is adjusted based on clearer characteristic portion information. Therefore, the synthetic three-dimensional information is created more accurately even on a wider measurement range.

One or more embodiments of the present invention is directed to an intraoral three-dimensional measurement result display method for creating images based on the wide range three-dimensional measurement information and the plurality of pieces of narrow range three-dimensional measurement information by the above-described intraoral three-dimensional measuring method and displaying, with a monitor, the images in an overlapping manner.

According to one or more embodiments of the present invention, the synthetic three-dimensional image is created while a state where the narrow range three-dimensional image is overlapped on the wide range three-dimensional image is displayed. Therefore, the user performs the synthesis operation while visually checking the synthesis state, and thus the synthetic three-dimensional information is created more accurately.

According to one or more embodiments of the present invention, the wide range three-dimensional measurement information and the plurality of pieces of narrow range three-dimensional measurement information displayed as the images in an overlapping manner may be displayed with at least one of brightness, color, luminance and display pattern being different between the images.

According to one or more embodiments of the present invention, the user clearly recognizes the narrow range three-dimensional image against the wide range three-dimensional image. Therefore, the synthetic three-dimensional information is created more accurately.

According to one or more embodiments of the present invention, the handy scanner may include a three-dimensional measurement element including a light source that emits projection light toward a measurement target; an image capturing element capturing an image of an area irradiated with the projection light; a guide path that guides light reflected by the measurement target toward the image capturing element; and a handheld housing that accommodates the light source, the guide path and the image capturing element.

The light source described above may be any of various light sources including a planar light source having a planar light emitting portion, a point light source having a point-like light emitting portion, and a strip light source having a strip-like light emitting portion. The light source may be a single light source or an array light source including a plurality of light sources. The light source may emit light that is shaped by a lens, an optical fiber, a light diffuser, a mask or the like. The light source may be a uniform light source emitting uniform project ion light or a structured light source emitting structured light having a sine waveform-like pattern, a lattice pattern or the like, or may include both of the uniform light source and the structured light source. The structured light source may include a mechanism dynamically changing the pattern of the structured projection light. The light source may be located such that the projection light passes the guide path or is directed directly toward the measurement target without passing the guide path.

In the case where a stereo method by use of a multiview camera is used as the three-dimensional measuring method, a plurality of image capturers may be used. In the case where any other method is used as the three-dimensional measuring method, a single image capturer may be used. The image capturer may be a CCD (Charge Coupled Device) image sensor using a photodiode, a CMOS (Complementary MOS) image sensor, or the like.

According to one or more embodiments of the present invention, three-dimensional on the measurement range in the narrow intraoral space is performed at high precision.

According to one or more embodiments of the present invention, the guide path may include a wide range guide path usable to measure the wide range; a narrow range guide path usable to measure the narrow range; and a switch that switches the guide path to the wide range guide path or to the narrow range guide path.

According to one or more embodiments of the present invention, one three-dimensional measurement element is usable to perform three-dimensional measurement on the entirety of the measurement range at high precision by merely switching the measurement range to the wide measurement range or to the narrow measurement range with a simple structure.

According to one or more embodiments of the present invention, a part of the housing may include an exchangeable unit that includes at least the guide path and is detachable and exchangeable to change the measurement range.

According to one or more embodiments of the present invention, one three-dimensional measurement element is usable to perform three-dimensional measurement on the entirety of the measurement range at high precision by merely switching the exchangeable unit to switch the measurement range to the wide measurement range or to the narrow measurement range.

The attachment error detector detecting an attachment error for the exchangeable unit, and the measurement result correction unit correcting the measurement result based on the attachment error, are further provided.

According to one or more embodiments of the present invention, the intraoral three-dimensional measuring device may further include an attachment that includes at least the guide path and is detachable from the housing to change the measurement range.

According to one or more embodiments of the present invention, one three-dimensional measurement element is usable to perform three-dimensional measurement on the entirety of the measurement range at high precision by merely detaching or attaching the attachment to switch the measurement range to the wide measurement range or to the narrow measurement range.

The attachment error detector detecting an attachment error for the attachment, and the measurement result correction unit correcting the measurement result based on the attachment error, are further provided.

According to one or more embodiments of the present invention, an intraoral three-dimensional measuring device and an intraoral three-dimensional measuring method can accurately perform three-dimensional measurement on a wide measurement range in an intraoral space, which is narrow, and also an intraoral three-dimensional measurement result can be displayed.

DETAILED DESCRIPTION OF EMBODIMENTS

Hereinafter, an intraoral three-dimensional measuring device 1 according to one or more embodiments of the present invention will be described with reference to FIG. 1 through FIG. 4E.

Figure 1:
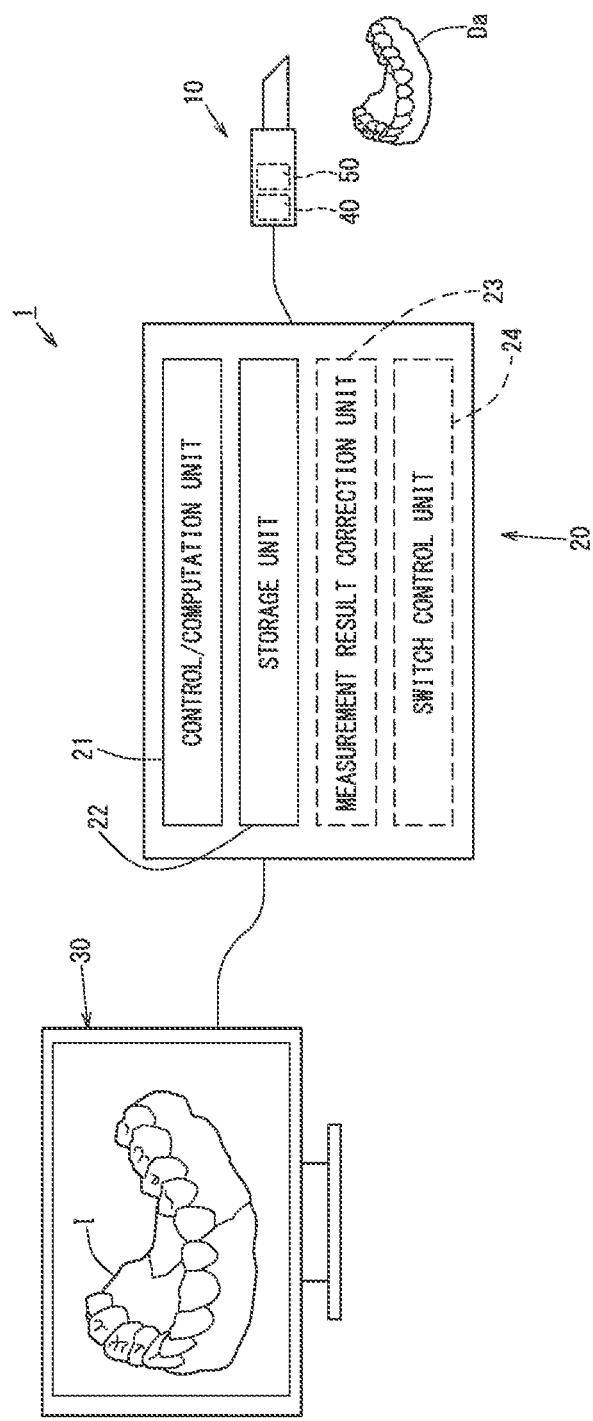
FIG. 1 is a schematic structural view of an intraoral three-dimensional measuring device.
Figure 2:
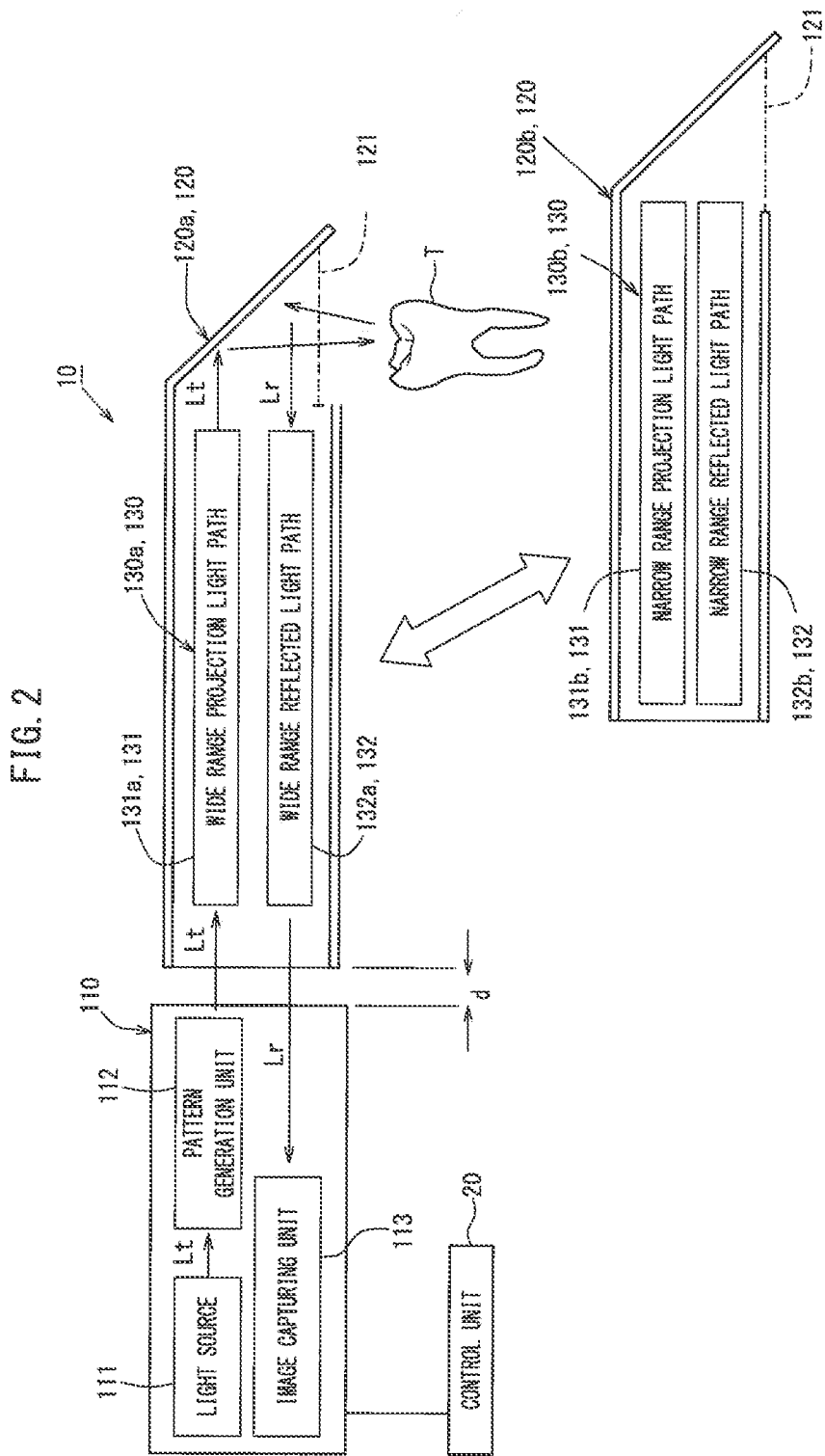
FIG. 2 is a schematic structural view of a handy scanner in an embodiment.
Figure 3:
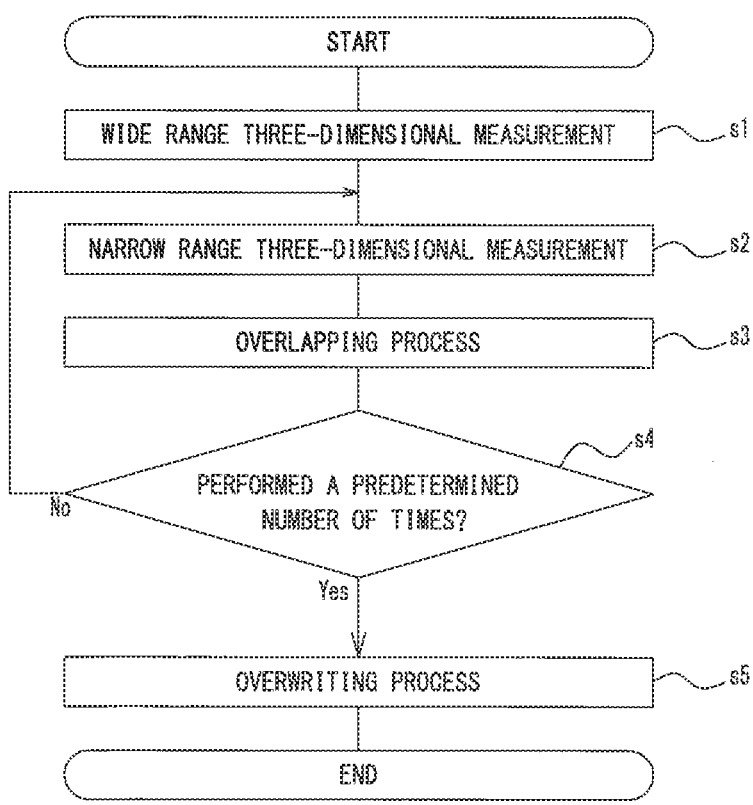
FIG. 3 is a flowchart showing an intraoral three-dimensional measuring method in an embodiment.

FIG. 1 is a schematic view of an intraoral three-dimensional measuring device 1. FIG. 2 is a schematic structural view of a handy scanner 10 (corresponding to a three-dimensional measuring element). FIG. 3 is a flowchart showing an intraoral three-dimensional measuring method. FIGS. 4A, 4B, 4C, 4D, and 4E show the intraoral three-dimensional measuring method.

Figure 4A:
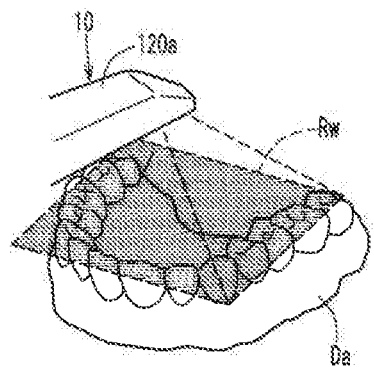
FIGS. 4A, 4B, 4C, 4D, and 4E show the intraoral three-dimensional measuring method.
Figure 4B:
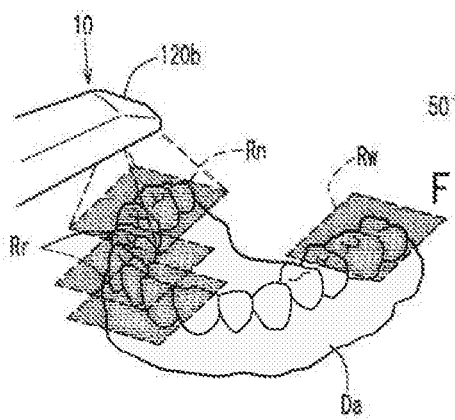
Figure 4C:
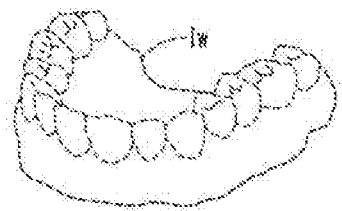
Figure 4D:
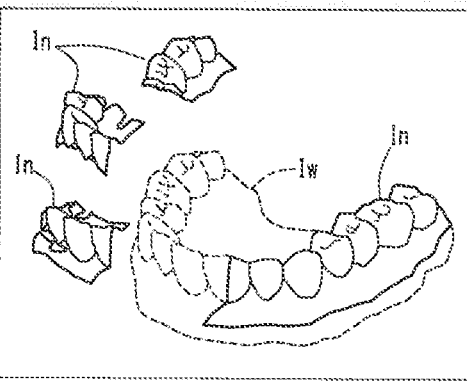
Figure 4E:
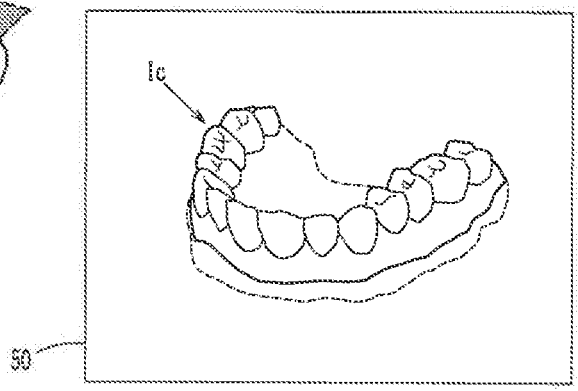

In more detail, FIG. 4A is an isometric view of a wide range three-dimensional measuring state, FIG. 4B is an isometric view of a narrow range three-dimensional measuring state, FIG. 4C shows a wide range three-dimensional image Iw (corresponding to wide range three-dimensional image information), FIG. 4D shows a state where narrow range three-dimensional images In (corresponding to narrow range three-dimensional image information) are overlapped on the wide range three-dimensional image Iw, and FIG. 4E shows a synthetic three-dimensional image Ic (corresponding to synthetic three-dimensional image information).

As shown in FIG. 1, the intraoral three-dimensional measuring device 1 is for measuring a three-dimensional shape of an intraoral dental arch Da, and includes a handy scanner 10, a control unit 20 and a monitor 30. The handy scanner 10 and the monitor 30 are connected with the control unit 20.

The handy scanner 10 includes a handheld housing main body 110 and a tip unit 120 (120a, 120b) (corresponding to an exchangeable unit) detachable from the housing main body 110.

The housing main body 110 accommodates a light source 111, a pattern generation unit 112, and an image capturing unit 113 (corresponding to an image capturing element). The pattern generation unit 112 converts projection light Lt, emitted from the light source 111 toward a tooth T as a measurement target, into structured light having a desirable pattern. The image capturing unit 113 captures an image of an area irradiated with the projection light Lt. The housing main body 110 is connected with the control unit 20 described below, and the light source 111, the pattern generation unit 112 and the image capturing unit 113 are controlled by a control/computation device 21 (controller) included in the control unit 20.

In this example, the pattern generation unit 112 is, for example, a slit mask including light transmissive portions and light blocking portions provided alternately in a periodical manner. After passing the pattern generation unit 112, the projection light Lt emitted by the light source 111 has a sinewave pattern. A combination of the light source 111 and the pattern generation unit 112 may be considered as a light source for structured light.

The light source 111 may be any of various light sources including a planar light source having a planar light emitting portion, a point light source having a point-like light emitting portion, and a strip light source having a strip-like light emitting portion. The light source 111 may be a single light source or an array light source including a plurality of light sources. The light source 111 may emit light that is shaped by a lens, an optical fiber, a light diffuser, a mask or the like.

In the case where the three-dimensional measuring method used by the intraoral three-dimensional measuring device 1 is a stereo method by use of a multiview camera, a plurality of image capturing units 113 are used. In the case where the three-dimensional measuring method used by the intraoral three-dimensional measuring device 1 is any other method, a single image capturing unit 113 is used. In this example, the intraoral three-dimensional measuring device 1 uses a phase shift method, and a single image capturing unit 113 is used.

The image capturing unit 113 may be a CCD (Charge Coupled Device) image sensor using a photodiode, a CMOS (Complementary MOS) image sensor, or the like. In FIG. 2, a light input/output opening 121 is on a bottom and tip side. Alternatively, the light input/output opening 121 may be at any side.

The tip unit 120 is detachable from a tip of the housing main body 110. The tip unit 120 includes a guide path 130. The guide path 130 guides the projection light Lt emitted from the light source 111 toward the tooth T or the like as the measurement target and also guides reflected light Lr reflected by the tooth T or the like. The tip unit 120 also includes the light input/output opening 121 at a bottom surface on the tip side. Via the light input/output opening 121, the projection light Lt is output toward the tooth T, and the reflected light Lr reflected by the tooth T is incident on the tip unit 120.

The guide path 130 includes a projection light path 131 usable to guide the projection light Lt and a reflected light path 132 usable to guide the reflected light Lr.

There are two types of tip unit 120. One is a wide range tip unit 120a usable to measure a wide range, and the other is a narrow range tip unit 120b usable to measure a range narrower than the wide range. The wide range tip unit 120a and the narrow range tip unit 120b are attachable to the housing main body 110 in an exchangeable manner.

The wide range tip unit 120a and the narrow unit tip unit 120b include different types of guide path 130. The wide range tip unit 120a includes a wide range guide path 130a usable to measure a wide range, and the narrow unit tip unit 120b includes a narrow range guide path 130b usable to measure a narrow range.

The wide range guide path 130a includes a wide range projection light path 131a and a wide range reflected light path 132a. The narrow range guide path 130b includes a narrow range projection light path 131b and a narrow range reflected light path 132b. The size of range to be measured may be adjusted by appropriately designing the positions, the focal distances and the number of lenses or any other optical element built in the guide path 130 of the tip unit 120.

The control unit 20 connected with the handy scanner 10 and the monitor 30 includes the control/computation device 21, and a storage unit 22.

The control/computation device 21 controls the light emission of the light source 111, a dynamic change in the pattern of the structured light to be projected (e.g., a shift in the phase of the structured light when the phase shift method is used, or a change in the focal position of the structured light when the focus method is used), or the image capturing of the image capturing unit 113. The control/computation device 21 also computes a three-dimensional shape based on the result of image capturing performed by the image capturing unit 113 to generate a three-dimensional measurement image. The storage unit 22 is connected with the control/computation device 21 and stores a control program or the like usable to control various data or devices connected thereto.

The monitor 30 is a display device such as a liquid crystal display device or the like, and is connected with the control unit 20. The monitor 30 is controlled by the control unit 20 to display a three-dimensional measurement image I or the like.

In FIG. 1, the control unit 20 and the handy scanner 10 have different housings. In the case where the entirety of, or a part of, the control unit 20 is sufficiently small, the control unit 20 may be accommodated in the housing main body 110 of the handy scanner 10.

The intraoral three-dimensional measuring device 1 having such a structure is used to accurately perform three-dimensional measurement on a wide measurement range in the narrow intraoral space by the intraoral three-dimensional measuring method. Hereinafter, the intraoral three-dimensional measuring method will be described with reference to FIG. 3 and FIG. 4.

In the following description, three-dimensional measurement will be performed on the entirety of the dental arch Da as the wide measurement range in the narrow intraoral space.

In this case, the wide range tip unit 120a including the wide range guide path 130a is attached to the housing main body 110 of the handy scanner 10. First, as shown in FIG. 4A, a wide range Rw including the entirety of the dental arch Da is subjected to three-dimensional measurement by the handy scanner 10 to acquire wide range three-dimensional measurement information (step s1 in FIG. 3). Based on the acquired wide range three-dimensional measurement information, the control/computation device 21 creates a wide range three-dimensional image Iw (FIG. 4C). The wide range three-dimensional image Iw is displayed on the monitor 30.

The wide range three-dimensional measurement information is acquired by the handy scanner 10 including the wide range tip unit 120a including the wide range guide path 130a and is on the entirety of the wide range Rw. Therefore, the information is of a low resolution, and the wide range three-dimensional image Iw created based on this information is also of a low resolution. The wide range three-dimensional image Iw often misses three-dimensional information of dead angles and thus is incomplete. In FIG. 4C, FIG. 4D and FIG. 4E, an image of a low resolution is represented by the dashed line, and an image of a high resolution described below is represented by the solid line.

Next, as shown in FIG. 4B, the narrow range tip unit 120b including the narrow range guide path 130b is attached to the housing main body 110 of the handy scanner 10 in replacement of the wide range tip unit 120a. A narrow range Rn including a small number of teeth T of the dental arch Da is subjected to three-dimensional measurement by the handy scanner 10 to acquire narrow range three-dimensional measurement information (step s2). Based on the acquired narrow range three-dimensional measurement information, the control/computation device 21 creates a narrow range three-dimensional image In.

The narrow range three-dimensional measurement information is acquired by the handy scanner 10 including the narrow range tip unit 130a including the narrow range guide path 130b and is on the narrow range Rn narrower than the wide range Rw. Therefore, the information is of a high resolution, and the narrow range three-dimensional image In created based on this information is also of a high resolution.

The narrow range three-dimensional image In created by the control/computation device 21 is displayed on the monitor 30 together with the wide range three-dimensional image Iw. More specifically, as shown in FIG. 4D, an overlapping process is performed (step s3).

In the overlapping step, the narrow range three-dimensional image In of a high resolution is overlapped on the wide range three-dimensional image Iw of a low resolution to create a synthetic three-dimensional image Ic.

In more detail, the overlapping process is as follows. Information on a characteristic portion (such information will be referred to as "characteristic portion information") included in the narrow range three-dimensional measurement information displayed as the narrow range three-dimensional image In, and information on a characteristic portion included in the wide range three-dimensional measurement information displayed as the wide range three-dimensional image Iw are compared against each other, and common characteristic portion information (corresponding to intra-measurement range position information) is extracted. By use of such common characteristic portion information, the narrow range three-dimensional measurement information of a high resolution (narrow range three-dimensional image In) is overlapped on the wide range three-dimensional measurement information of a low resolution (wide range three-dimensional image Iw).

Such an overlapping process of overlapping the narrow range three-dimensional image In of a high resolution on the wide range three-dimensional image Iw of a low resolution to create the synthetic three-dimensional image Ic (step s3) is performed a plurality of times in repetition while the number of repetition has not reached a predetermined number of times (step s4: No) until the entirety of the dental arch Da is covered.

In the overlapping process shown in FIG. 4D, a plurality of narrow range three-dimensional images In of right back portions of the dental arch Da are overlapped on the wide range three-dimensional image Iw of the entirety of the dental arch Da.

When the overlapping process of overlapping the narrow range three-dimensional image In on the wide range three-dimensional image Iw is performed the predetermine number of times, namely, when the plurality of narrow range three-dimensional images In are overlapped on the entirety of the wide range three-dimensional image Iw (step s4: Yes), information on each of parts of the wide range three-dimensional image Iw is overwritten with the corresponding narrow range three-dimensional image In. Thus, the synthetic three-dimensional image Ic is created (step s5).

The handy scanner 10 may include a position information acquisition unit 40 such as a GPS or the like acquiring position information on the three-dimensional measurement information (wide range three-dimensional measurement information, narrow range three-dimensional measurement information) to be acquired. In this case, based on the acquired position information (position information acquisition step), synthetic three-dimensional information (synthetic three-dimensional image Ic) in which the position of each piece of narrow range three-dimensional measurement information (narrow range three-dimensional image In) is adjusted with respect to the wide range three-dimensional measurement information (wide range three-dimensional image Iw) is created.

In the above description, the wide range tip unit 120a or the narrow range tip unit 120b is attached to the housing main body 110 in an exchangeable manner. The hand scanner 10 may include an attachment error detection unit 50 (FIG. 1) detecting an attachment error d (FIG. 2) between the tip unit 120 and the housing main body 110 at the time of exchange. In this case, the control unit 20 may include a measurement result correction unit 23 (FIG. 1) correcting a three-dimensional measurement result based on the attachment error d detected by the attachment error detection unit 50.

In the above description, the wide range tip unit 120a or the narrow range tip unit 120b is attached to the housing main body 110 in an exchangeable manner. Alternatively, as shown in FIG. 5, an attachment 120c including an additional guide path 130c may be attached to the wide range tip unit 120a, so that a combination of the wide range tip unit 120a and the attachment 120c is used instead of the narrow range tip unit 120b.

Figure 5:
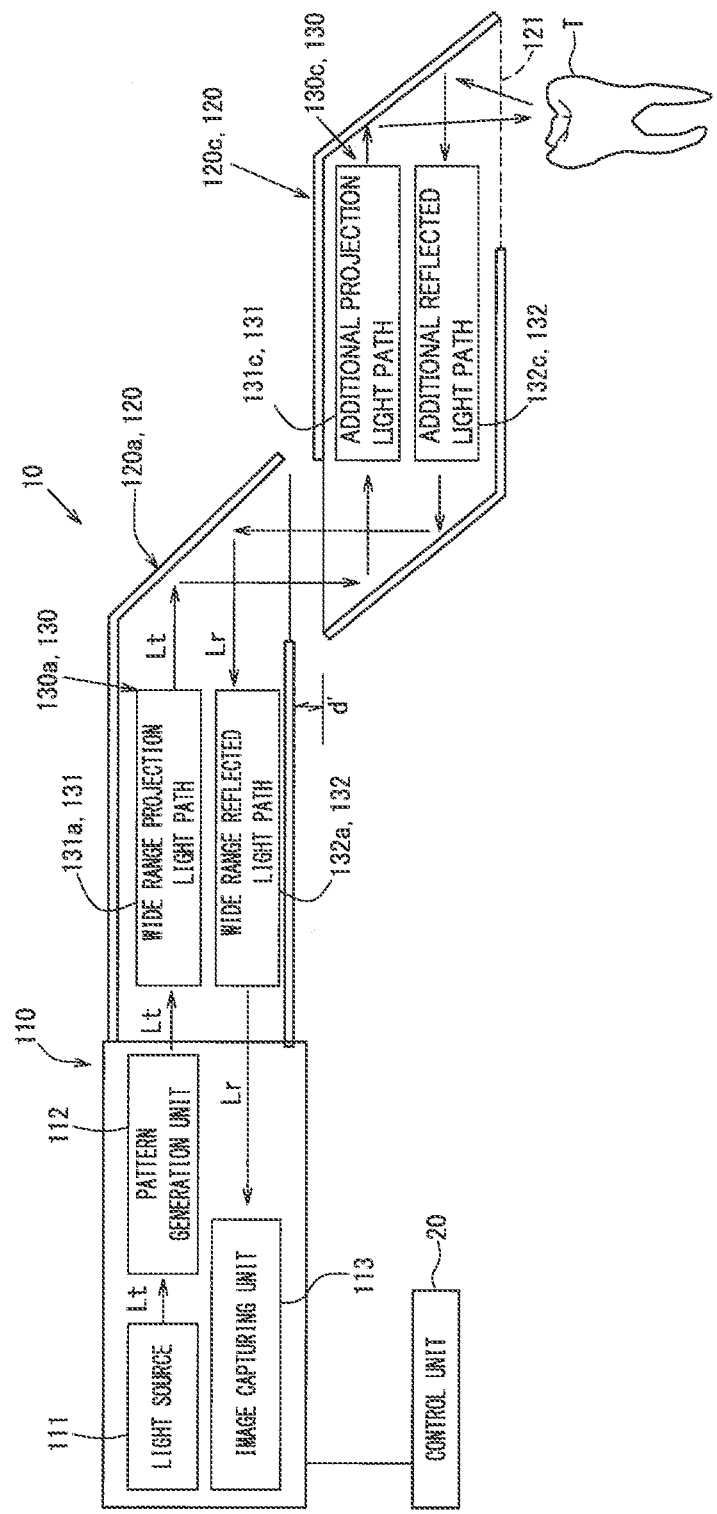
FIG. 5 is a schematic structural view of a handy scanner in another embodiment.

In FIG. 5, the attachment 120c includes the light input/output opening 121 at the bottom surface on the tip side, like the tip unit 120. Alternatively, the light input/output opening 121 may be at any side. The additional guide path 130c includes an additional projection light path 131c and an additional reflected light path 132c, like the wide range guide path 130a.

In FIG. 5, a combination of the wide range tip unit 120a and the attachment 120c is used in place of the narrow range tip unit 120b. Alternatively, a combination of the narrow range tip unit 120b and an attachment may be used in place of the wide range tip unit 120a. The size of range to be measured may be adjusted by appropriately designing the positions, the focal distances and the number of lenses or any other optical element built in the guide paths in the tip unit and the attachment.

The attachment 120c may include an attachment error detection unit detecting an attachment error d' (FIG. 5) between the wide range tip unit 120a and the attachment 120c. In this case also, the control unit 20 may include a measurement result correction unit 23 correcting a three-dimensional measurement result based on the attachment error d' detected by the attachment error detection unit 50.

Figure 6:
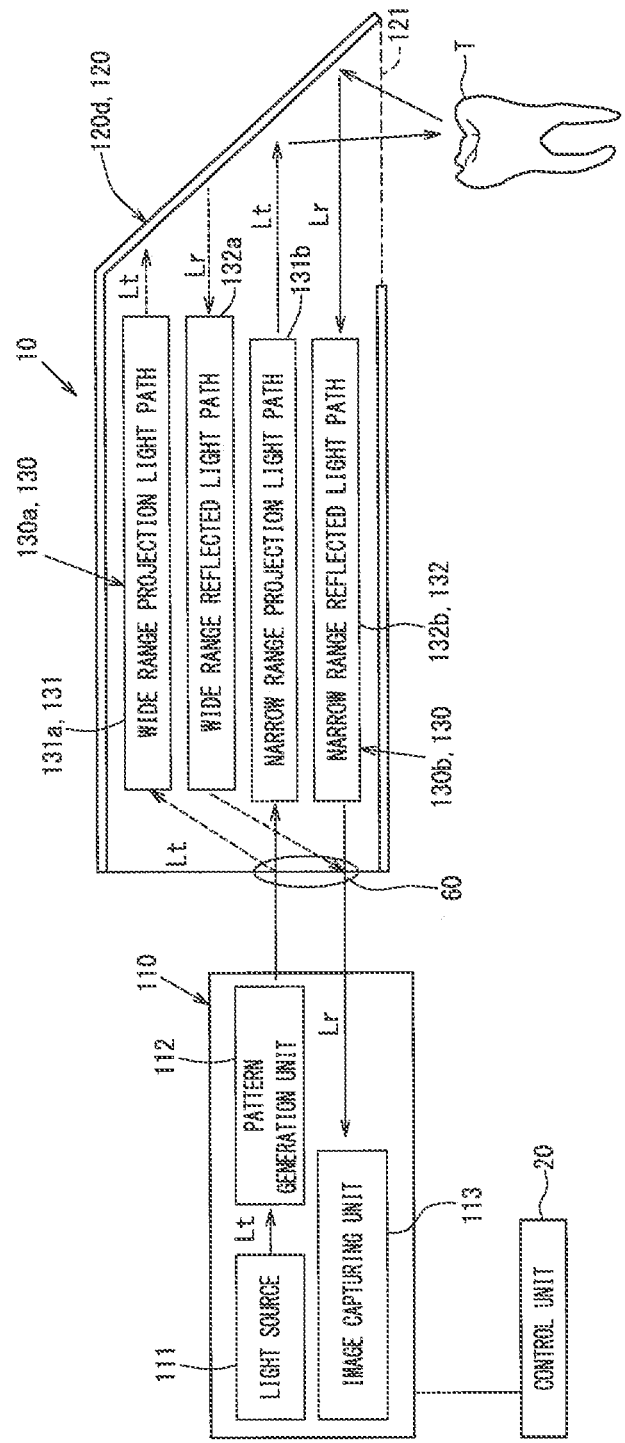
FIG. 6 is a schematic structural view of a handy scanner instill another embodiment.

As shown in FIG. 6, a tip unit 120d may be attached to the housing main body 110. The tip unit 120d includes the wide range guide path 130a, the narrow range guide path 130b, and an optical path switching unit 60 switching the optical path. The optical path switching unit 60 is, for example, a mirror. In this case, the control unit 20 may include a switch control unit 24 (FIG. 1) controlling the optical path switching unit 60 to switch the optical path.

In the example shown in FIG. 6, the tip unit 120d includes the wide range guide path 130a and the narrow range guide path 130b located side by side, and the optical path is switched by the optical path switching unit 60. Alternatively, the tip unit 120d may include the wide range guide path 130a and the additional guide path 130c included in the attachment 120c coupled with each other in series. In this case, the optical switching unit 60 switches between a state where the light is guided by the additional guide path 130c and a state where the light is not guided by the additional guide path 130c. The size of range to be measured may be adjusted by appropriately selecting the positions, the focal distances and the number of lenses or any other optical element built in the guide path 130 by the switching operation.

Figure 7:
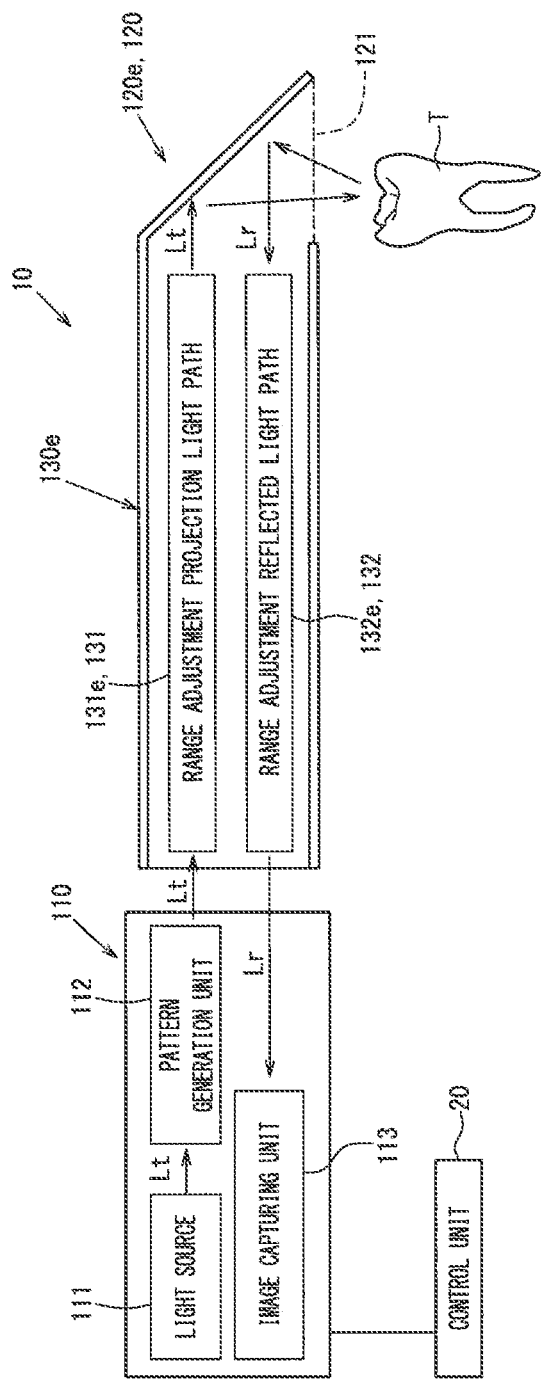
FIG. 7 is a schematic structural view of a handy scanner instill another embodiment.

As shown in FIG. 7, the handy scanner 10 may include a tip unit 120e including a range adjustment guide path 130e (including a range adjustment projection light path 131e and a range adjustment reflected light path 132e). The range adjustment guide path 130e adjusts the measurement range from the wide range to the narrow range by, for example, using a focal distance adjusting optical element such as a variable-focus lens (e.g., liquid lens), a spatial light modulator, a deformable mirror or the like, or mechanically moving a lens or the like included in the guide path.

In the above description, after all the narrow range three-dimensional images In are overlapped on the wide range three-dimensional images Iw (step s4: Yes), the information on each part of the wide range three-dimensional image Iw is overwritten with the corresponding narrow range three-dimensional image In (step s5). Alternatively, after each narrow range three-dimensional image In is overlapped on the wide range three-dimensional image Iw (step s3), the information on the corresponding part of the wide range three-dimensional image Iw may be overwritten with the narrow range three-dimensional image In.

In the above description, the wide range Rw including the entirety of the dental arch Da is subjected to three-dimensional measurement to acquire the wide range three-dimensional measurement information, and the wide range three-dimensional image Iw is created based on the wide range three-dimensional measurement information. Alternatively, the dental arch Da may be divided into a plurality of wide ranges, which are subjected to three-dimensional measurement.

Figure 8:
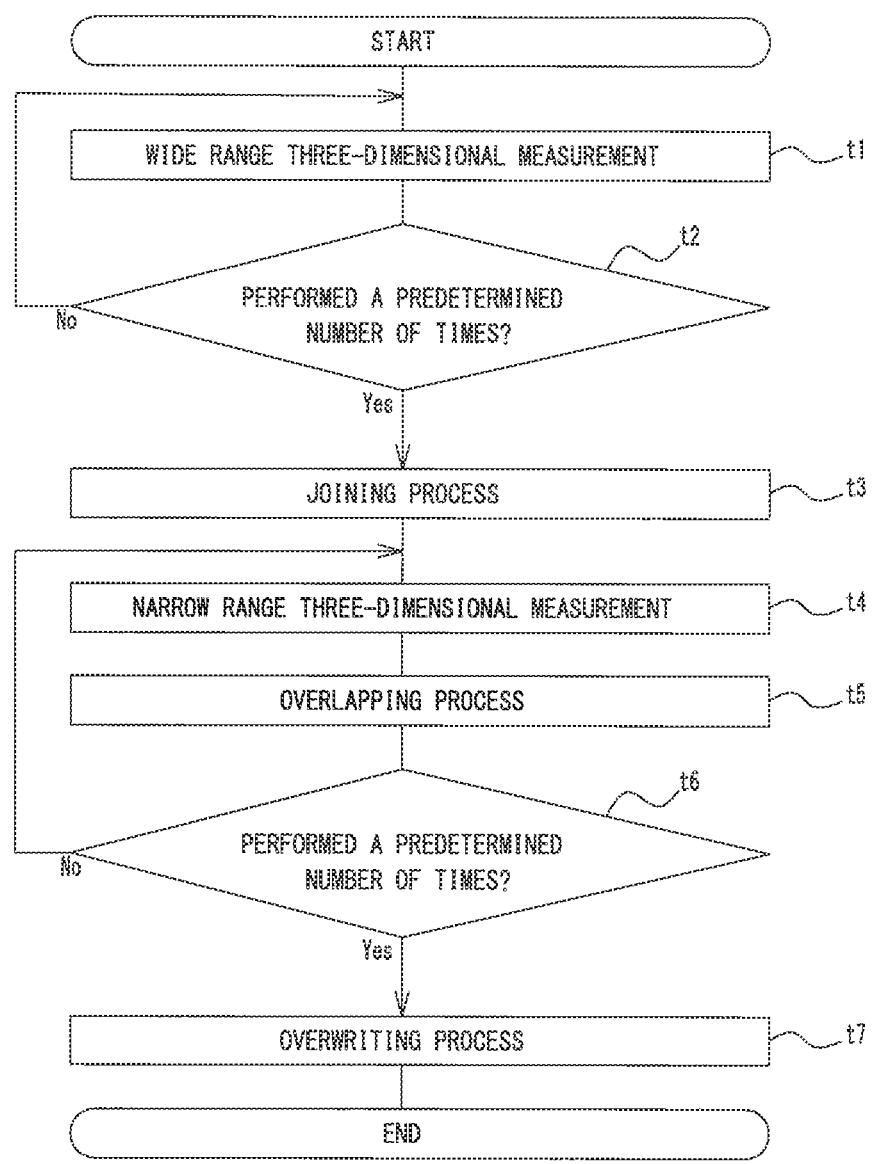
FIG. 8 is a flowchart showing an intraoral three-dimensional measuring method in another embodiment.

In this case, the measurement is performed as shown in FIG. 8. The wide range tip unit 120a including the wide range guide path 130a is attached to the housing main body 110 of the handy scanner 10. A wide range including a part of the dental arch Da is subjected to three-dimensional measurement by the handy scanner 10 to acquire wide range three-dimensional measurement information (step t1).

Such a step is performed in repetition while the number of repetition has not reached a predetermined number of times (step t2: No). As a result of the step being repeated the predetermined number of times (step t2: Yes), the wide range three-dimensional measurement information on the entirety of the dental arch Da is acquired. For this step, a plurality of wide ranges are set so as to cover the entirety of the dental arch Da and so as to include overlap portions Rr.

Such a wide range Rr is apart of the dental arch Da but is wider than the narrow range Rn. Therefore, the number of times by which such a wide range is subjected to three-dimensional measurement to measure the entirety of the dental arch Da is smaller than the number of times by which the narrow range Rn is subjected to three-dimensional measurement to measure the entirety of the dental arch Da.

Then, the acquired plurality of pieces of wide range three-dimensional measurement information are joined together by use of, as a joining reference, three-dimensional measurement information on the overlap portions Rr (step t3). As a result, entire joining measurement information on the entirety of the dental arch Da is created.

Based on the entire joining measurement information, the control/computation device 21 creates a wide range three-dimensional image Iw. In the meantime, a narrow range Rn is subjected to three-dimensional measurement to acquire narrow range three-dimensional measurement information. Based on the acquired narrow range three-dimensional measurement information, the control/computation device 21 creates a narrow range three-dimensional image In (step t4). Then, an overlapping process is performed (step t5); more specifically, the narrow range three-dimensional image In is overlapped on the wide range three-dimensional image Iw to create a synthetic three-dimensional image Ic. Such an overlapping process is performed in repetition while the number of repetition has not reached a predetermined number of times (step t6: No).

When the overlapping process of overlapping the narrow range three-dimensional image In on the wide range three-dimensional image Iw is performed the predetermine number of times, namely, when the plurality of narrow range three-dimensional images In are overlapped on the entirety of the wide range three-dimensional image Iw (step t6: Yes), the information on each of parts of the wide range three-dimensional image Iw is overwritten with the corresponding narrow range three-dimensional image In. Thus, the synthetic three-dimensional image Ic is created (step t7).

In the step of joining the plurality of pieces of wide range three-dimensional measurement information to create the entire joining measurement information and creating the wide range three-dimensional image Iw based on the entire joining measurement information, the entire joining measurement information may be adjusted based on narrow range three-dimensional measurement information including information on parts corresponding to the overlap portions Rr. The information on such parts is usable as the joining reference.

Figure 9:
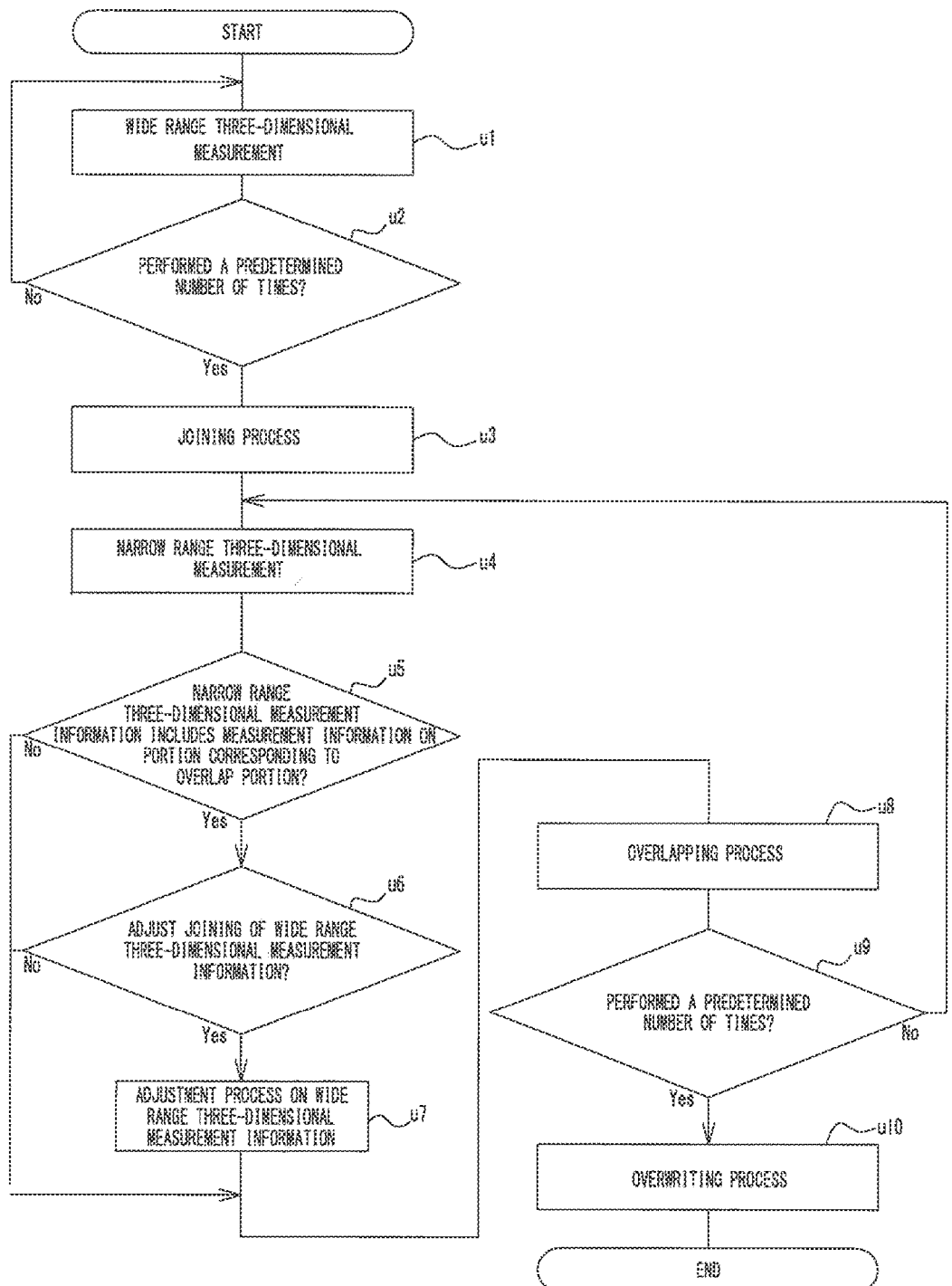
FIG. 9 is a flowchart showing an intraoral three-dimensional measuring method in still another embodiment.

In this case, the measurement is performed as shown in FIG. 9. First, steps u1 through u3 corresponding to step t1 through t3 in FIG. 8 are performed to create entire joining measurement information on the entirety of the dental arch Da.

Then, the narrow range tip unit 120b including the narrow range light path 130b is attached to the housing main body 110 of the handy scanner 10. A narrow range Rn including a plurality of teeth T of the dental arch Da is subjected to three-dimensional measurement by the handy scanner 10 to acquire narrow range three-dimensional measurement information (step u4). In the case where acquired narrow range three-dimensional measurement information includes measurement information on a part corresponding to an overlap portion Rr, usable as the joining reference (step u5: Yes), it is determined whether or not the joining of the corresponding parts of the wide range three-dimensional measurement information is to be adjusted based on the narrow range three-dimensional measurement information (corresponding to adjustment narrow range three-dimensional measurement information) including the measurement information on the part corresponding to the overlap portion Rr. When it is determined to perform adjustment (step u6: Yes), the adjustment is performed, and thus post-adjustment entire joining measurement information is created (step u7). The narrow range three-dimensional measurement information is overlapped on the post-adjustment entire joining measurement information to create synthetic three-dimensional information (step u8).

In the case where the acquired narrow range three-dimensional measurement information does not include measurement information on the part corresponding to the overlap portion Rr (step u5: No), or it is determined that the joining of the corresponding parts of the wide range three-dimensional measurement information is not to be adjusted (step u6: No), the narrow range three-dimensional measurement information is overlapped on the entire joining measurement information (step u8). Such an operation is performed in repetition while the number of repetition has not reached a predetermined number of times (step u9: No). When the narrow range three-dimensional measurement information is overlapped on the entirety of the entire joining measurement information (step u9: Yes), the entire joining measurement information is overwritten with the narrow range three-dimensional measurement information to create a synthetic three-dimensional image Ic (step u10).

There may be an operation mode in which even if the condition for terminating the repetition in each of steps s4, t2, t6, u2 and u9, the user terminates the measurement by pressing a termination button or the like to create the three-dimensional image Ic or Iw although being incomplete.

There may be an operation mode by which the user resumes the measurement from the middle of the repetition in each of steps s4, t2, t6, u2 and u9 by pressing a resume switch or the like.

Figure 10:
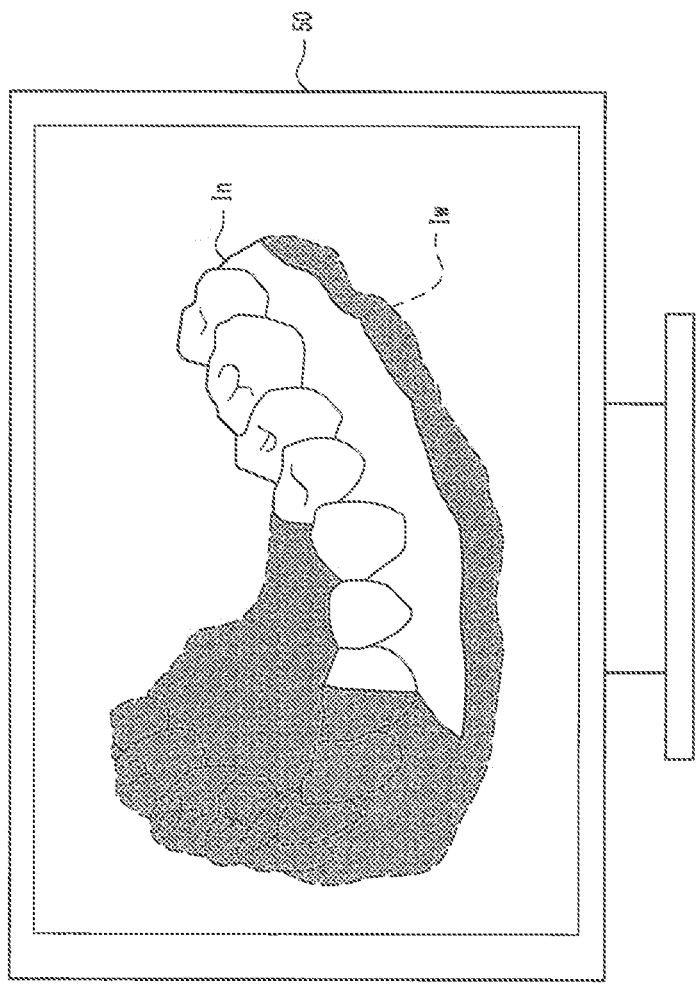
FIG. 10 is a schematic view showing an intraoral three-dimensional measurement result display method.
Figure 11A:
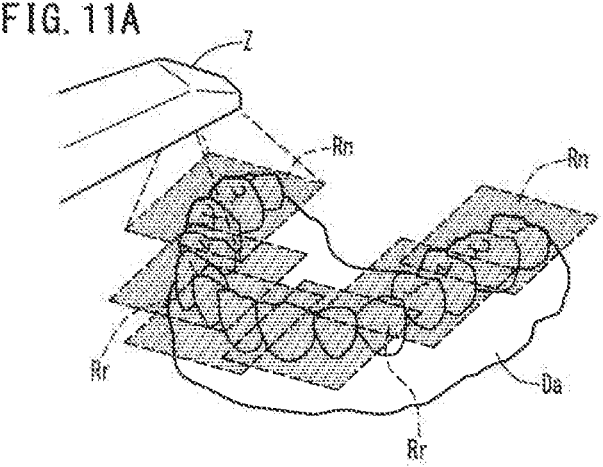
FIGS. 11A, 11B, 11C, and 11D show a conventional intraoral three-dimensional measuring method.
Figure 11B:
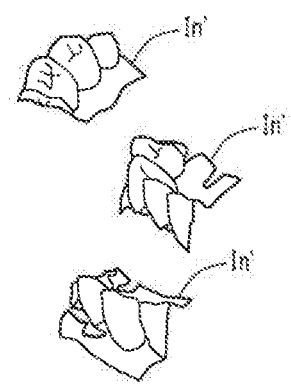
Figure 11C:
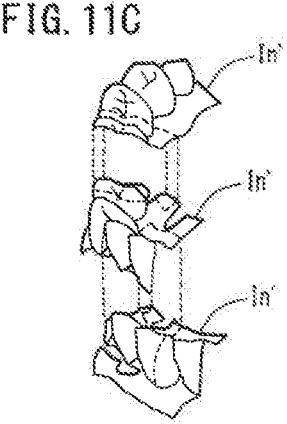
Figure 11D:
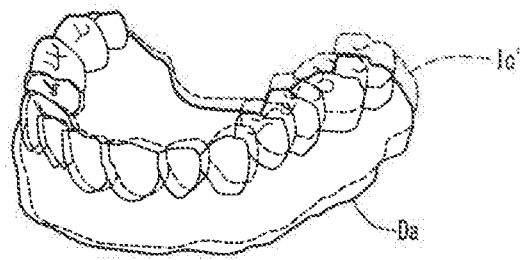

In the above description, the narrow range three-dimensional image In of a high resolution is overlapped on the wide range three-dimensional image Iw of a low resolution. Alternatively, as shown in FIG. 10, for example, the wide range three-dimensional image Iw of a low resolution may be displayed at a low brightness, or the narrow range three-dimensional image In of a high resolution may be displayed at a high brightness. The wide range three-dimensional image Iw and the narrow range three-dimensional image In may be displayed with color, luminance or display pattern (e.g., in a continuously lit up state, or a blinked state) being different between the images. Needless to say, the brightness, color, luminance, display pattern and any other manner of display may be varied in combination.

In the above description, the measurement target is the entirety of the dental arch Da. Alternatively, the measurement target may be, for example, a part of the dental arch Da.

As described above, the intraoral three-dimensional measuring device 1 is used to perform a wide range three-dimensional measurement information acquisition step (step s1, t1, u1), a narrow range three-dimensional measurement information acquisition step (step s2, t4, u4), and a synthetic three-dimensional information creation step (step s3, t5, u8). In the wide range three-dimensional measurement information acquisition step, a three-dimensional shape of the wide range Rw including the dental arch Da, which is a desirable measurement range in an intraoral space, is measured to acquire wide range three-dimensional measurement information. In the narrow range three-dimensional measurement information acquisition step, three-dimensional shapes of the narrow ranges Rn, which are narrower than the wide range Rw, are measured to acquire a plurality of pieces of narrow range three-dimensional measurement information. In the synthetic three-dimensional information creation step, the plurality of pieces of narrow range three-dimensional measurement information are located based on the wide range three-dimensional measurement information to create synthetic three-dimensional information on the measurement range. In this step, each piece of narrow range three-dimensional measurement information is located by use of, as a synthesis reference, intra-measurement range position information (characteristic portion information) common to the wide range three-dimensional measurement information and the narrow range three-dimensional measurement information. The synthetic three-dimensional information on the measurement range created in this manner includes the narrow range three-dimensional measurement information based on the wide range three-dimensional measurement information. The accumulation of errors, which occurs in the conventional measuring device Z, is not caused. Thus, three-dimensional measurement on the dental arch Da, which is a wide measurement range in the narrow intraoral space, is accurately performed.

The wide range three-dimensional measurement information acquired by measurement on the three-dimensional shape of the wide range Rw is used to create the wide range three-dimensional image Iw. The narrow range three-dimensional measurement information acquired by measurement on the three-dimensional shape of the narrow range Rn is used to create the narrow range three-dimensional images In. In the synthetic three-dimensional information creation step (step s3, t5, u8), the synthetic three-dimensional image Ic is created based on the synthetic three-dimensional information. In this manner, the measurement information on the entirety of the measurement range is displayed as an image. This allows the user to make an operation while visually checking the measurement results, and thus improves the operability.

In the narrow range three-dimensional measurement information acquisition step (step s2, t4, u4), the narrow range three-dimensional measurement information is acquired at a higher resolution than that of the wide range three-dimensional measurement information. Therefore, the resultant synthetic three-dimensional information (synthetic three-dimensional image Ic) of the measurement range includes the narrow range three-dimensional measurement information of a high resolution based on the wide range three-dimensional measurement information with no accumulation of errors. Thus, three-dimensional measurement on the entirety of the measurement range is performed at a high resolution.

When the narrow range three-dimensional measurement information (narrow range three-dimensional image In) is located on the wide range three-dimensional measurement information (wide range three-dimensional image Iw), the part of the wide range three-dimensional measurement information corresponding to the narrow range three-dimensional measurement information is overwritten with the narrow range three-dimensional measurement information (step s5, t7, u10). Therefore, the information amount of the synthetic three-dimensional information is decreased.

The wide range three-dimensional measurement information is acquired by measurement on the shape of the entirety of the dental arch Da. The resultant synthetic three-dimensional information is more accurate than synthetic three-dimensional information created in the case where a plurality of pieces of information on ranges narrower than the wide range Rw and wider than the narrow range Rn are joined together at overlapping portions to provide wide range three-dimensional measurement information on the entirety of the measurement range.

The wide range three-dimensional image Iw (wide range three-dimensional measurement information) and the narrow range three-dimensional image In (narrow range three-dimensional measurement information) both created by the above-described intraoral three-dimensional measuring method may be displayed on the monitor in an overlapping manner. In this case, the synthetic three-dimensional image Ic is created while a state where the narrow range three-dimensional image In is overlapped on the wide range three-dimensional image Iw is displayed. Therefore, the synthesis operation is performed while the synthesis state is visually checked, and thus the synthetic three-dimensional information is created more accurately.

The handy scanner 10 includes the light source 111; the pattern generation unit 112 converting the projection light Lt, emitted from the light source 111 toward the tooth T as a measurement target, into structured light having a desirable pattern; the guide path 130 (130a, 130b, 130c, 130e) guiding the projection light Lt emitted from the light source 111 toward the dental arch Da and also guiding the reflected light Lr reflected by the dental arch Da; the image capturing unit 113 capturing an area irradiated with the projection light Lt; and the handheld housing main body 110 accommodating the light source 111, the pattern generation unit 112 and the image capturing unit 113. Therefore, three-dimensional measurement on a measurement range in the narrow intraoral space is performed at high precision.

The handy scanner 10 may use the wide range tip unit 120a or the narrow range tip unit 120b in an exchangeable manner to change the measurement range. The wide range tip unit 120a and the narrow range tip unit 120b are detachable from the housing main body 110. In this case, the measurement range is switched to the wide measurement range or to the narrow measurement range by merely exchanging the tip unit 120. One handy scanner 10 is usable to perform three-dimensional measurement on the entirety of the measurement range at high precision.

Preferably, the attachment error detection unit 50 detecting an attachment error d between the tip unit 120a or 120b and the housing main body 110, and the measurement result correction unit 23 correcting the measurement result based on the attachment error d, are further provided.

As shown in FIG. 5, the handy scanner 10 may use the attachment 120c. The attachment 120c includes the additional guide path 130c and is attachable to the wide range tip unit 120a, attached to the housing main body 110, to change the measurement range. In this case, the measurement range is switched to the wide measurement range or the narrow measurement range by merely attaching or detaching the attachment 120c. One handy scanner 10 is usable to perform three-dimensional measurement on the entirety of the measurement range at high precision.

Preferably, the attachment error detection unit 50 detecting an attachment error d' between the attachment 120c and the housing main body 110, and the measurement result correction unit 23 correcting the measurement result based on the attachment error d', are further provided.

As shown in FIG. 6, the handy scanner 10 may use the tip unit 120d including the optical path switching unit 60 switching the guide path to the wide range guide path 130a usable to measure the wide range or to the narrow range guide path 130b usable to measure the narrow range. In this case, one handy scanner 10 is usable to perform three-dimensional measurement on the entirety of the measurement range at high precision by merely switching the measurement range to the wide measurement range or to the narrow measurement range with a simple structure.

The handy scanner 10 may include the position information acquisition unit 40, so that the position information acquisition step is performed. In the position information acquisition step, the position information on each of the narrow range three-dimensional measurement information and the wide range three-dimensional measurement information is acquired. In the synthetic three-dimensional information creation step (step s3, t5, u8), the synthetic three-dimensional information is adjusted based on the position information acquired in the position information acquisition step. The resultant synthetic three-dimensional information is more precise and more accurate.

As shown in FIG. 8, an entire joining measurement information creation step (step t3, u3) may be performed. In the entire joining measurement information creation step, a plurality of pieces of wide range three-dimensional measurement information are located by use of, as the joining reference, wide range position information common to adjacent pieces of wide range three-dimensional measurement information, to create the entire joining measurement information on the entirety of the measurement range. In this case, the synthetic three-dimensional information is created more accurately even on a wider measurement range.

As shown in FIG. 9, at least one of the plurality of narrow range three-dimensional measurement information is used as narrow range three-dimensional measurement information (adjustment narrow range three-dimensional measurement information) including information on the part corresponding to the overlap portion Rr, which is usable as the joining reference. Before the synthetic three-dimensional information creation step (step s3, t5, u8), an entire joining measurement information adjustment step (step u7) may be performed. In the entire joining measurement information adjustment step, the entire joining measurement information is adjusted based on the narrow range three-dimensional measurement information (adjustment narrow range three-dimensional measurement information). In this case, the entire joining measurement information is adjusted based on clearer characteristic portion information. Therefore, the synthetic three-dimensional information is created more accurately even on a wider measurement range.

As shown in FIG. 10, the wide range three-dimensional image Iw and the narrow range three-dimensional image In may be displayed on the monitor 30 in an overlapping manner with at least one of brightness, color, luminance and display pattern being different between the two types of images. In this case, the narrow range three-dimensional image In is clearly recognizable against the wide range three-dimensional image Iw. Therefore, the synthetic three-dimensional information is created more accurately.

The wide range three-dimensional measurement information acquisition step according to one or more embodiments of the present invention corresponds to step s1, t1 or u1 in the above-described embodiment. Similarly, the narrow range three-dimensional measurement information acquisition step corresponds to step s2, t4 or u4;

the synthetic three-dimensional information creation step corresponds to step s3, t5 or u8;

the wide range three-dimensional image information corresponds to the wide range three-dimensional image Iw;

the narrow range three-dimensional image information corresponds to the narrow range three-dimensional image In;

the synthetic three-dimensional image information corresponds to the synthetic three-dimensional image Ic;

the overwriting process corresponds to step s5, t7 or u10;

the entire joining measurement information creation step corresponds to step t3 or u3;

the adjustment narrow range three-dimensional measurement information corresponds to the narrow range three-dimensional measurement information including information on a part corresponding to the overlap portion Rr;

the entire joining measurement information adjustment step corresponds to step u7;

the measurement information acquisition unit and the three-dimensional measuring element each correspond to the handy scanner 10;

the synthetic three-dimensional information creation unit corresponds to the control/computation device 21;

the position information acquisition unit corresponds to the position information acquisition unit 40;

the measurement target corresponds to the dental arch Da;

the guide path corresponds to the guide path 130, the wide range guide path 130a, the narrow range guide path 130b, the additional guide path 130c, or the range adjustment guide path 130e;

the image capturing element corresponds to the image capturing unit 113;

the wide range guide path corresponds to the wide range guide path 130*a*;

the narrow range guide path corresponds to the narrow range guide path 130*b*;

the switching unit corresponds to the optical path switching unit 60; and the exchangeable unit corresponds to the wide range tip unit 120*a* or the narrow range tip unit 120*b*.

The present invention is not limited to the above-described embodiment, and may be carried out in any of many various embodiments.

For example, in the above description, the desirable measurement range is the dental arch Da. Alternatively, the desirable measurement range may be a part of the dental arch Da, or the entirety of, or a part of, edentulous jaw.

The above-described position information is not limited to being acquired by the position information acquisition unit 40 such as a GPS or the like, and may be acquired by a position sensor measuring a relative position with respect to the intraoral space. Alternatively, the position information may be acquired by an acceleration sensor, a velocity sensor, a gyro sensor, an azimuthal sensor, a posture sensor, or a combination of any of these sensors.

The handy scanner 10 may include a light source for illumination instead of, or in addition to, the light source 111.

In the above description, in the state where the narrow range three-dimensional measurement information (narrow range three-dimensional image In) is overlapped on the wide range three-dimensional measurement information (wide range three-dimensional image Iw), the part of the wide range three-dimensional measurement information corresponding to the narrow range three-dimensional measurement information is overwritten with the narrow range three-dimensional measurement information (step s5, t7, u10). Alternatively, the narrow range three-dimensional measurement information may be merely overlapped on the wide range three-dimensional measurement information, but the wide range three-dimensional measurement information does not need to be overwritten with the narrow range three-dimensional measurement information.

EXPLANATION OF REFERENCES

1 . . . Intraoral three-dimensional measuring device
10 . . . Handy scanner
21 . . . Control/computation device
40 . . . Position information acquisition unit
60 . . . Optical path switching unit
110 . . . Housing main body
111 . . . Light source
112 . . . Pattern generation unit
113 . . . Image capturing unit
120, 120*d*, 120*e* . . . Tip unit
120*a* . . . Wide range tip unit
120*b* . . . Narrow range tip unit
120*c* . . . Attachment
130 . . . Guide path
130*a* . . . Wide range guide path
130*b* . . . Narrow range guide path
130*c* . . . Additional guide path
130*e* . . . Range adjustment guide path
Da . . . Dental arch
Ic . . . Synthetic three-dimensional image
In . . . Narrow range three-dimensional image
Iw . . . Wide range three-dimensional image
Lr . . . Reflected light
Lt . . . Projection light

What is claimed is:

1. An intraoral three-dimensional measuring method, comprising:

acquiring, with a handy scanner, wide range three-dimensional measurement information on a three-dimensional shape measured on a wide range in a desirable measurement range in an intraoral space;

acquiring, with the handy scanner, a plurality of pieces of narrow range three-dimensional measurement information each on a three-dimensional shape measured on a narrow range narrower than the wide range in the measurement range; and locating, with a controller, the plurality of pieces of narrow range three-dimensional measurement information based on the wide range three-dimensional measurement information by use of, as a synthesis reference, intra-measurement range position information common to the wide range three-dimensional measurement information and each of the plurality of pieces of narrow range three-dimensional measurement information, and creating synthetic three-dimensional information on the measurement range, wherein the creating comprises:
overwriting a part of the wide range three-dimensional measurement information corresponding to each piece of narrow range three-dimensional measurement information with each piece of narrow range three-dimensional measurement information.

2. The intraoral three-dimensional measuring method according to claim 1, wherein the wide range three-dimensional measurement information is used to create wide range three-dimensional image information on the three-dimensional shape of the wide range, the plurality of pieces of narrow range three-dimensional measurement information are each used to create narrow range three-dimensional image information on the three-dimensional shape of the narrow range, and the creating creates synthetic three-dimensional image information based on the synthetic three-dimensional information.

3. The intraoral three-dimensional measuring method according to claim 1, wherein the acquiring measures the plurality of pieces of narrow range three-dimensional measurement information at a higher resolution than that of the wide range three-dimensional measuring information.

4. The intraoral three-dimensional measuring method according to claim 1, wherein the creating creates the synthetic three-dimensional information by use of, as intra-measurement range position information, characteristic portion information common to each of the plurality of pieces of narrow range three-dimensional measurement information and the wide range three-dimensional measurement information.

5. The intraoral three-dimensional measuring method according to claim 1, further comprising:

acquiring, with the handy scanner, position information on each of the plurality of pieces of narrow range three-dimensional measurement information and position information on the wide range three-dimensional measurement information, wherein the creating comprises:
adjusting the synthetic three-dimensional information based on the acquired position information.

6. The intraoral three-dimensional measuring method according to claim 1, wherein the wide range three-dimensional measurement information is entire measurement information on a shape of the entirety of the measurement range.

7. An intraoral three-dimensional measuring method comprising:
  acquiring, with a handy scanner, wide range three-dimensional measurement information on a three-dimensional shape measured on a wide range in a desirable measurement range in an intraoral space;
  acquiring, with the handy scanner, a plurality of pieces of narrow range three-dimensional measurement information each on a three-dimensional shape measured on a narrow range narrower than the wide range in the measurement range;
  locating, with a controller, the plurality of pieces of narrow range three-dimensional measurement information based on the wide range three-dimensional measurement information by use of, as a synthesis reference, intra-measurement range position information common to the wide range three-dimensional measurement information and each of the plurality of pieces of narrow range three-dimensional measurement information, and creating synthetic three-dimensional information on the measurement range, and
  locating, with the controller, a plurality of pieces of the wide range three-dimensional measurement information by use of, as a joining reference, wide range position information common to adjacent pieces of wide range three-dimensional measurement information, and creating entire joining measurement information on the entirety of the measurement range.

8. The intraoral three-dimensional measuring method according to claim 7, wherein
  at least one of the plurality of pieces of the narrow range three-dimensional measurement information is adjustment narrow range three-dimensional measurement information including measurement information on a part corresponding to the wide range position information, and
  the intraoral three-dimensional measuring method further comprises:
  adjusting, with the controller, the entire joining measurement information based on the adjustment narrow range three-dimensional measurement information located in the synthetic three-dimensional information.

9. An intraoral three-dimensional measurement result display method comprising:
  creating, with the controller, images based on the wide range three-dimensional measurement information and the plurality of pieces of narrow range three-dimensional measurement information by the intraoral three-dimensional measuring method according to claim 1; and
  displaying, with a monitor, the images in an overlapping manner.

10. The intraoral three-dimensional measurement result display method according to claim 9, wherein the wide range three-dimensional measurement information and the plurality of pieces of narrow range three-dimensional measurement information displayed as the images in an overlapping manner are displayed with at least one of brightness, color, luminance and display pattern being different between the images.

11. An intraoral three-dimensional measurement result display method comprising:
  creating, with the controller, images based on the wide range three-dimensional measurement information and the plurality of pieces of narrow range three-dimensional measurement information by the intraoral three-dimensional measuring method according to claim 7; and
  displaying, with a monitor, the images in an overlapping manner.

12. An intraoral three-dimensional measuring device, comprising:
  a handy scanner that acquires
    wide range three-dimensional measurement information on a three-dimensional shape measured on a wide range in a desirable measurement range in an intraoral space, and
    a plurality of pieces of narrow range three-dimensional measurement information each on a three-dimensional shape measured on a narrow range narrower than the wide range in the measurement range; and
  a controller that locates the plurality of pieces of narrow range three-dimensional measurement information based on the wide range three-dimensional measurement information by use of, as a synthesis reference, intra-measurement range position information common to the wide range three-dimensional measurement information and each of the plurality of pieces of narrow range three-dimensional measurement information, and creates synthetic three-dimensional information on the measurement range,
  wherein the handy scanner comprises:
    a light source that emits projection light toward a measurement target;
    an image capturing element that captures an image of an area irradiated with the projection light;
    a guide path that guides light reflected by the measurement target toward the image capturing element; and
    a handheld housing that accommodates the light source, the guide path, and the image capturing element, and
  wherein a part of the housing comprises an exchangeable unit that comprises at least the guide path and is detachable and exchangeable to change the measurement range.

13. The intraoral three-dimensional measuring device according to claim 12, wherein
  the wide range three-dimensional measurement information is usable to create wide range three-dimensional image information on the three-dimensional shape of the wide range,
  the plurality of pieces of narrow range three-dimensional measurement information each are usable to create narrow range three-dimensional image information on the three-dimensional shape of the narrow range, and
  the controller creates synthetic three-dimensional image information based on the synthetic three-dimensional information.

14. The intraoral three-dimensional measuring device according to claim 12, wherein the plurality of pieces of narrow range three-dimensional measurement information are measured at a higher resolution than that of the wide range three-dimensional measuring information.

15. The intraoral three-dimensional measuring device according to claim 12, wherein the controller creates the synthetic three-dimensional information by use of, as the intra-measurement range position information, characteristic portion information common to the each of plurality of pieces of narrow range three-dimensional measurement information and the wide range three-dimensional measurement information.

16. The intraoral three-dimensional measuring device according to claim 12, wherein
the handy scanner acquires position information on each of the plurality of pieces of narrow range three-dimensional measurement information and acquiring position information on the wide range three-dimensional measurement information, and
the controller adjusts the synthetic three-dimensional information based on the acquired position information.

17. The intraoral three-dimensional measuring device according to claim 12, wherein the guide path comprises:
a wide range guide path usable to measure the wide range;
a narrow range guide path usable to measure the narrow range; and
a switch that switches the guide path to the wide range guide path or to the narrow range guide path.

18. An intraoral three-dimensional measuring device comprising:
a handy scanner that acquires
wide range three-dimensional measurement information on a three-dimensional shape measured on a wide range in a desirable measurement range in an intraoral space, and
a plurality of pieces of narrow range three-dimensional measurement information each on a three-dimensional shape measured on a narrow range narrower than the wide range in the measurement range; and
a controller that locates the plurality of pieces of narrow range three-dimensional measurement information based on the wide range three-dimensional measurement information by use of, as a synthesis reference, intra-measurement range position information common to the wide range three-dimensional measurement information and each of the plurality of pieces of narrow range three-dimensional measurement information, and creates synthetic three-dimensional information on the measurement range,
wherein the handy scanner comprises:
a light source that emits projection light toward a measurement target;
an image capturing element that captures an image of an area irradiated with the projection light;
a guide path that guides light reflected by the measurement target toward the image capturing element; and
a handheld housing that accommodates the light source, the guide path, and the image capturing element,
wherein the intraoral three-dimensional measuring device further comprises an attachment that comprises at least the guide path,
wherein the attachment is detachable from the housing to change the measurement range.

* * * * *